United States Patent [19]

Helms et al.

[11] Patent Number: 5,425,771
[45] Date of Patent: Jun. 20, 1995

[54] BONE REPLACEMENT PART MADE OF GLASS IONOMER CEMENT

[75] Inventors: Jan Helms; Götz Geyer, both of Würzburg; Erich Wanek, Seefeld; Werner Zöllner, Oberpfaffenhofen; Oswald Gasser, Seefeld, all of Germany

[73] Assignee: Thera Patent GmbH & Co. KG Gesellschaft fur industrielle Schutzrechte, Seefeld, Germany

[21] Appl. No.: 191,216
[22] Filed: Feb. 3, 1994

Related U.S. Application Data

[60] Division of Ser. No. 862,204, Apr. 2, 1992, Pat. No. 5,314,474, which is a continuation of Ser. No. 489,826, Mar. 9, 1990, abandoned.

[30] Foreign Application Priority Data

Mar. 9, 1989 [DE] Germany ............. 39 07 663.6

[51] Int. Cl.⁶ ............................................. A61F 2/28
[52] U.S. Cl. .......................................... 623/16; 623/66
[58] Field of Search ....................... 623/16, 66

[56] References Cited

U.S. PATENT DOCUMENTS

| | | |
|---|---|---|
| 3,814,717 | 6/1974 | Wilson et al. |
| 4,250,277 | 2/1981 | Maries et al. |
| 4,360,605 | 11/1982 | Schmitt et al. ............ 523/116 |
| 4,366,253 | 12/1982 | Yagi. |
| 4,376,835 | 3/1983 | Schmitt et al. |
| 4,518,430 | 5/1985 | Brown et al. ............ 623/16 |
| 4,527,979 | 7/1985 | McLean et al. |
| 4,591,384 | 5/1986 | Akashane et al. ............ 106/35 |
| 4,758,612 | 7/1988 | Wilson et al. ............ 524/5 |
| 4,797,431 | 1/1989 | Billington et al. ............ 523/116 |
| 4,861,808 | 8/1989 | Billington et al. ............ 523/116 |
| 4,900,697 | 2/1990 | Akashane et al. ............ 501/57 |
| 4,927,866 | 5/1990 | Purrmann et al. |
| 5,084,491 | 1/1992 | Kerby ............ 523/116 |
| 5,120,340 | 6/1992 | Duchlyne et al. ............ 623/16 |

FOREIGN PATENT DOCUMENTS

| | | |
|---|---|---|
| 931294 | 7/1973 | Canada. |
| 0241277 | 10/1087 | European Pat. Off. |
| 0023013 | 1/1981 | European Pat. Off. |
| 0024056 | 2/1981 | European Pat. Off. |
| 2061513 | 6/1971 | Germany. |
| 2319715 | 10/1973 | Germany. |
| 2905183.C3 | 2/1979 | Germany. |
| 3248357 | 7/1984 | Germany. |

OTHER PUBLICATIONS

Council on Dental Materials and Devices, *State Report on Glass Ionomer Cements*, JADA, vol. 99, pp. 221–226, Aug. 1979.

Kent et al., *The Properties of a Glass Ionomer Cement*, British Dental Journal, 1973, vol. 135, pp. 322–326.

*Primary Examiner*—David H. Willse
*Assistant Examiner*—Bruce Snow
*Attorney, Agent, or Firm*—Foley & Lardner

[57] ABSTRACT

Bone replacement parts consisting of glass ionomer cement are superior to those made of ceramics especially since they may easily be produced and machined using common grinding and milling tools. The required prosthesis part may therefore be formed of freshly mixed glass ionomer cement during the respective operation, or an industrially prefabricated formed body approximating the idealized shape of the bone part to be replaced may be adapted to the anatomic conditions given.

20 Claims, No Drawings

BONE REPLACEMENT PART MADE OF GLASS IONOMER CEMENT

This application is a division of application Ser. No. 07/862,204, filed Apr. 2, 1992, now U.S. Pat. No. 5,314,474, which is a continuation of Ser. No. 07/489,826 filed Mar. 9, 1990, now abandoned.

BACKGROUND OF THE INVENTION

Bone structures or bone parts in the human body may be destroyed due to inflammatory processes, malignant tumors or traumatic events; they may be replaced by suitable prostheses. Apart from metals, which are used to replace highly strained bone structures, ceramic prostheses serve for replacing less strained bone structures, such as in the region of the head. Ceramic materials are used in this region for reconstructing, e.g., parts of the auditory ossicle chain, of the auditory walls or even of the jaw.

Prosthetic parts must be adapted to the given individual dimensions and conditions. This is difficult to be done with ceramic prostheses due to their complicated workability. Consequently, dimensional adjustability is a chief requirement in the design of ceramic protheses, whereas given natural anatomic conditions can take into account only to a minor extent. A single-piece middle ear prosthesis designed according to this concept is described, e.g., in German Patent Specification 2,905,183.

Heterologous bone grafts, which are equally employed, are not always available and have proven to be problematic in view of possible HIV infections.

SUMMARY OF THE INVENTION

It is an object of the present invention to provide bone structures, specifically bone replacement parts, made of body-tolerated material which are readily manufactured extracorporeally to the shape and size of the bone part to be replaced or fitted from prefabricated parts.

This object is met by a bone replacement part, which is made of a non-foamed glass ionomer cement.

The glass ionomer cement may specifically include the following constituents:

(a) a calcium and/or strontium aluminium fluorosilicate glass powder containing 20 to 60 wt-% $SiO_2$, 10 to 50 wt-% $Al_2O_3$, 0 to 40 wt-% CaO, 0 to 40 wt-% SrO, 1 to 40 wt-% F, 0 to 10 wt-% $Na_2O$ and 0 to 10 wt-% $P_2O_5$, with a minimum of 1 wt-% CaO and/or SrO, (b) a polycarboxylic acid having an average molecular weight of 1.000 to 20.000, in a concentration of 5 to 50 wt-% related to constituent (a), (c) water, and optionally (d) tartaric acid as a chelate-former.

In a preferred embodiment, constituent (a) contains 25 to 50 wt-% $SiO_2$, 10 to 40 wt-% $Al_2O_3$, 0 to 35 wt-% CaO, 0 to 35 wt-% SrO, 5 to 30 wt-% F, 0 to 8 wt-% $Na_2O$ and 1 to 10 wt-% $P_2O_5$, with a minimum of 10 wt-% CaO and/or SrO. Specifically preferred are contents of 25 to 45 wt-% $SiO_2$, 20 to 40 wt-% $Al_2O_3$, 10 to 30 wt-% CaO, 10 to 30 wt-% F, 1 to 8 wt-% $Na_2O$ and 1 to 10 wt-% $P_2O_5$.

The bone replacement structures according to the invention consist of a compact, i.e. non-foamed, glass ionomer cement and are formed outside the body, which is in contrast to the conventional dental use of glass ionomer cements. It is thus possible to shape the bone replacement part intra-operatively from freshly mixed glass ionomer cement, let it cure outside the body and subsequently implant the cured part. According to an alternative method, industrially prefabricated formed bodies having a shape approximating that of the bone structure to be replaced in an idealizing manner may also be adapted to the anatomic conditions. In contrast to ceramic material, no problems arise in finishing glass ionomer cement formed bodies by means of the usual cutting methods.

The replacement parts according to the invention may be readily obtained by plastically deforming a mixed cement mass which will cure within a few minutes to form a rigid part and may then be machined mechanically by means of usual grinding or milling instruments. Moreover, the cured part will chemically combine with the freshly mixed and still plastic cement so that replacement parts in accordance with the invention may easily be secured in situ. It as an advantage that glass ionomer cements combine to form a chemical bond with the body's hard tissues such as bones.

Moreover, the replacement parts according to the invention are very bio-compatible or bio-active, i.e. they are not enclosed by connective tissue. Instead, new bone growth is facilitated in direct bone contact due to the presence of a replacement part according to the invention.

The easy formability and workability permits individual shaping so that the bone replacement structures are capable of reproducing the respective natural bone in an idealized shape.

The term "formed body" used in this specification will be understood to include also granulates which are implanted to fill a bone defect.

DESCRIPTION OF PREFRRED EMBODIMENTS

The bio-mimetic bone structures formed extra-corporeally from non-foamed glass ionomer cement in accordance with the invention are suited for the following applications:

(1) Ear
  Outer ear
    auricular frame replacement
  Middle ear
    idealized incus
    idealized malleus
    idealized stapes
    TORP (Total Ossicular Replacement Prosthesis)
    PORP (Partial Ossicular Replacement Prosthesis)
    crescent-shaped structure for reconstructing the tympanic frame
    partial or total replacement of the posterior auditory conduit wall
    utilization in mastoid obliterations (closure of the temporal bone).

(2) Lateral base of the cranium
  Covering a defect of the middle and posterior cranial fossa.

(3) Cranium
  Replacement in case of calotte defects.

(4) Frontobase
  Reconstruction of bony frontobase defects inclusive of the posterior wall of the frontal sinus and dural lesions.

(5) Replacement of cranial bones especially in
  cranium base defects and
  cranium dome defects replacement of facial bone defects in the middle face, e.g. of the bony nose frame, frontal bone, frontal sinus wall, nasal septum, orita base, orita dome, and front wall of the maxillary sinus general replacement of bone substance and stabilization of middle face bridges, with a possible combination with conventionally utilized plates.

(6) Larynx

Implants for stabilizing and replacing the trachea and the larynx (7) Jaw surgery alveolar appendix hard palate replacement of jaw parts, particularly in the lower jaw replacement of bone defects, for stabilization and osteosynthesis in LeFort fractures as facial bone pads in plastic surgery Glass ionomer cements substantially consist of the following constituents: p1 (a) a glass or metal oxide which forms, by acid decomposition, metal ions causing cross-linkage of (b), (b) a polymer poly acid, with the acid functions being sulphonic, phosphonic or carboxylic acids, (c) water, and optionally (d) a chelate-former.

In addition, stabilizers, disinfectants, pigments, X-ray contrast media and other fillers may be contained.

The glass ionomer cements are available as mixtures of glass and a polymer poly acid, on the one hand, and water, on the other hand, with the chelate-former being optionally admixed to one of the two constituents. It is equally possible to dissolve the polymer poly acid in water, admix the optional chelate-former and mix this solution with the glass.

In addition to glass powders containing calcium, magnesium or lanthanum as specified in German Offenlegungsschriften 2,061,513 and 3,248,357, and glass powders containing strontium according to Published European Patent Application 0,241,277, glass powders comprising other cations may be employed. Calcium- and/or strontium-fluorcsilicate glasses are prefered so that the aluminium fluorosilicate glass powders may comprise the following constituents in addition to oxygen:

| constituent | calculated as | weight percent |
|---|---|---|
| Si | $SiO_2$ | 20 to 60 |
| Al | $Al_2O_3$ | 10 to 50 |
| Ca | CaO | 0 to 40 |
| Sr | SrO | 0 to 40 |
| F | F | 1 to 40 |
| Na | $Na_2O$ | 0 to 10 |
| P | $P_2O_5$ | 0 to 10 |

At least 1 wt-% CaO and/or SrO must be contained. Further, a total of 0 to 20 wt-%, calculated as oxides, of B, Bi, Zn, Mg, Sn, Ti, Zr, La or other trivalent lanthanides, K, W, Ge as well as other additives may be contained which do not impair the properties and are physiologically harmless. The glasses may be made visible in X-rays by addition of 10 to 20 wt-% of $La_2O_3$.

The powder particles preferably consist of

| Si as $SiO_2$ | 25 to 50 wt-% |
|---|---|
| Al as $Al_2O_3$ | 10 to 40 wt-% |
| Ca as CaO | 0 to 35 wt-% |
| Sr as SrO | 0 to 35 wt-% |
| F | 5 to 30 wt-% |
| Na as $Na_2O$ | 0 to 8 wt-% |
| P as $P_2O_5$ | 1 to 10 wt-% |

At least 10 wt-% Ca (calculated as CaO) and/or Sr (calculated as SrO) must be contained. Further, 0 to 10 wt-% of $B_2O_3$, $Bi_2O_3$, ZnO, MgO, $SnO_2$, $TiO_2$, ZrO, $La_2O_3$ or other oxides of trivalent lanthanides, $K_2O$, $WO_3$, $GeO_2$ as well as other additives are possible which do not impair the properties and are physiologically harmless.

Particularly preferred powders contain:

| Si as $SiO_2$ | 25 to 45 wt-% |
|---|---|
| Al as $Al_2O_3$ | 20 to 40 wt-% |
| Ca as CaO | 10 to 30 wt-% |
| F | 10 to 30 wt-% |
| Na as $Na_2O$ | 1 to 8 wt-% |
| P as $P_2O_5$ | 1 to 10 wt-% |

Examples of the preferred compositions are listed in the following TABLE:

TABLE

| | (wt-%) | | | |
|---|---|---|---|---|
| | A | B | C | D |
| Si as $SiO_2$ | 35.0 | 27.6 | 29.0 | 45.4 |
| Al as $Al_2O_3$ | 30.4 | 26.0 | 25.1 | 35.0 |
| Ca as CaO | 14.9 | 28.8 | 24.6 | 10.1 |
| F | 17.7 | 17.0 | 23.0 | 10.3 |
| Na as $Na_2O$ | 2.7 | 2.1 | 2.2 | 6.9 |
| P as $P_2O_5$ | 6.9 | 8.3 | 5.8 | 2.4 |

The glass powder particles utilized in accordance with the invention may be calcium or strontium depleted at their surfaces, as described for calcium in European Patent Application 0,023,013.

The glass powders employed in accordance with the invention have an average grain size (weight average) of at least 1 μm, preferably 3 μm at least. The average grain size (weight average) is 1 to 20 μm, preferably 3 to 15 μm, especially preferably 3 to 10 μm. The particles have a maximum grain size of 150 μm, preferably 100 μm, especially preferably 60 μm. A not too narrow grain size distribution is favourable for attaining good mechanical properties, the distribution being obtained by milling and removing the coarse parts by screening.

The polymer poly acids used as constituent (b) may be polycarboxylic acids, e.g. polymaleic acid, polyacrylic acid, polyitaconic acid as well as mixtures thereof or copolymers, particularly the maleic-itaconic acid copolymers and/or the acrylic-itaconic acid copolymers known from European Patent application 0,024,056 as known in the production of glass ionomer cement powders. The average molecular weight of the polycarboxylic acids used is more than 500. An average molecular weight is preferably between 1.000 and 20.000, the range of 3.000 to 10.000 being especially preferred. The polycarboxylic acid is preferably employed in a concentration of 5 to 50 wt-% related to constituent (a).

Known chelate-forming additives (cf. German Offenlegungsschrift 2,319,715) may be used as constituent (d) in the glass ionomer cement in accordance with the invention. Tartaric acid is preferably employed as a chelate-former.

EXAMPLE 1

250 parts by weight of a calcium aluminium fluorosilicate glass powder having the composition A of the above TABLE are mixed with 100 parts by weight of a solution consisting of 37 parts of a copolymer (1:1) of acrylic acid and maleic acid, 9 parts tartaric acid and 54 parts water.

A bone structure for replacing a posterior auditory wall may be formed manually from the pasty material thus obtained. The replacement part is completely cured after 10 minutes and may be applied in situ with freshly mixed and still plastic cement.

The bone replacement will be incorporated with no problem three weeks after the operation and there will be no gaps in the structure.

EXAMPLE 2

Formed bodies of 15mm×20mm×5mm are produced from the material mixed according to Example 1 and implanted in the left tibia of a baboon. The implant does not differ from the bone material on X-ray images. Two weeks later, marked bone formation activity at the implant edge appears, and after another four weeks, the implant has been completely surrounded by newly formed bone material and the spot does no longer differ from the surrounding bone material as.

EXAMPLE 3

An idealized auditory ossicle (incus) having a rounded shape as shown in the attached drawing is produced from the mixed cement of Example 1. Rounded shapes are more bio-compatible than the sharp-edged bodies such as formed of ceramics. The danger of perforating the tympanum is minimized; epithelial cells preferably grow over round shapes.

EXAMPLE 4

The formed body according to Example 2 is worked by means of milling instruments common in ENT-surgery, and an idealized incus is formed thereof. It may easily be worked without causing cracks, chippings or fractures in the formed body.

What is claimed is:

1. A method for producing an implant for replacing defective bone parts, the implant having a predetermined shape, which comprises the steps of:
   i) shaping a non-foamed, non-porous, glass ionomer cement which comprises:
      (a) an aluminum fluorosilicate glass which forms by acid decomposition, metal ions causing cross-linking of (b),
      (b) a polymer containing acid groups selected from the group consisting of sulphonic, phosphonic, and carboxylic acid, and
      (c) water, into said implant intra-operatively or extracorporally, and
   ii) curing the shaped part extracorporally.
2. A method of claim 1, which further comprises iii) implanting the cured part into the body.
3. A method of claim 1, wherein step i) takes place intra-operatively.
4. A method of claim 1, wherein step i) takes place extracorporally.
5. A method of claim 2, wherein step i) takes place intra-operatively.
6. A method of claim 2, wherein step i) takes place extracorporally.
7. A method of claim 1, wherein the cement further comprises a chelate-former (d).
8. A method of claim 1, wherein (a) comprises a glass powder selected from the group consisting of the oxides of calcium, magnesium, lanthium, strontium, and mixtures of at least two of these metals.
9. A method of claim 1, wherein (a) comprises an aluminum fluorosilicate glass powder selected from the group consisting of calcium and strontium containing
   20 to 60 wt-% $SiO_2$,
   10 to 50 wt-% $Al_2O_3$,
   0 to 40 wt-% CaO,
   0 to 40 wt-% SrO,
   1 to 40 wt-% F,
   0 to 10 wt-% $Na_2O$, and
   0 to 10 wt%-% $P_2O_5$,
   with a minimum of 1 wt-% of CaO if said powder is said calcium aluminum fluorosilicate or with a minimum of 1 wt-% SrO if said powder is said strontium aluminum fluorosilicate, and
   (b) comprises a polycarboxylic acid having an average molecular weight of more than 500 and is present in a concentration of 5 to 50 wt-% related to constituent (a).
10. A method of claim 1, wherein component (a) comprises:
    25 to 50 wt-% $SiO_2$,
    10 to 40 wt-% $Al_2O_3$,
    0 to 35 wt-% CaO,
    0 to 35 wt-% SrO,
    5 to 30 wt-% F,
    0 to 8 wt-% $Na_2O$, and
    1 to 10 wt%-% $P_2O_5$,
    with a minimum of 10 wt-% CaO if said powder is said calcium aluminum fluorosilicate or with a minimum of 10 wt-% SrO if said powder is said strontium aluminum fluorosilicate.
11. A method of claim 10, wherein component (a) comprises:
    25 to 45 wt-% $SiO_2$,
    20 to 40 wt-% $Al_2O_3$,
    10 to 30 wt-% CaO,
    10 to 30 wt-% F,
    1 to 8 wt-% $Na_2O$, and
    1 to 10 wt%-% $P_2O_5$.
12. A method of claim 8, wherein the average grain size of the glass powder is 1 to 20 μm and wherein the maximum grain size of the glass powder is 150 μm.
13. A method of claim 1, wherein component (b) has an average molecular weight of 1,000 to 20,000.
14. A method of claim 1, wherein component (b) is selected from the group consisting of polymaleic acid, polyacrylic acid, polyitaconic acid, maleic-itaconic acid copolymers, acrylic-itaconic acid copolymers, acrylic-maleic acid copolymers, and mixtures of at least two of these polymers.
15. A method of claim 1, wherein said cement further comprises an additive selected from the group consisting of stabilizers, disinfectants, pigments, x-ray contrast media, fillers other than the previously recited additives, and mixtures of at least one of these additives.
16. A method of claim 7, wherein the chelate former is tartaric acid.
17. A method of claim 9, wherein component (a) further comprises 0 to 20 wt. % of oxides of metals selected from the group consisting of B, Bi, Zn, Mg, Sm, Ti, Zr, La, trivalent lanthanides other than said Sm, K, W, Ge, and mixtures of at least one of these oxides.
18. A method of claim 4, wherein said shaping comprising one or both of grinding and milling.
19. A method of claim 1, wherein said implant is a prosthesis for an ear, cranium, larynx, or jaw bone.
20. A method of claim 4, wherein said implant is a prosthesis for an ear, cranium, larynx, or jaw bone.

* * * * *